United States Patent [19]
Gupta et al.

[11] Patent Number: 6,115,489
[45] Date of Patent: Sep. 5, 2000

[54] SYSTEM AND METHOD FOR PERFORMING IMAGE-BASED DIAGNOSIS

[75] Inventors: Rajiv Gupta, New York, N.Y.; Christopher James Dailey, Mc Gill, Nev.; Valtino Xavier Afonso, Des Plaines, Ill.; Rasiklal Punjalal Shah, Latham, N.Y.

[73] Assignee: General Electric Company, Schenectady, N.Y.

[21] Appl. No.: 08/921,959

[22] Filed: Sep. 2, 1997

[51] Int. Cl.$^7$ ........................................................ G06K 9/00
[52] U.S. Cl. ............................ 382/141; 382/152; 382/157
[58] Field of Search .................................... 382/152, 157, 382/141; 348/130; 364/474.21, 474.34; 702/34, 35

[56] References Cited

U.S. PATENT DOCUMENTS 5,838,816  11/1998  Holmberg ................................ 382/157
5,926,558   7/1999  Zelt, III et al. ......................... 382/152

*Primary Examiner*—Amelia Au
*Assistant Examiner*—Vikkram Bali
*Attorney, Agent, or Firm*—Dave Goldman; Jill M. Breedlove

[57] ABSTRACT

The present invention discloses a system and method for performing image-based diagnosis. In this invention, historical artifact images and corresponding actions for repairing the artifacts are acquired and stored in a database. The database of historical artifact images and corresponding actions is used to diagnose an incoming artifact image having an unknown fault.

18 Claims, 5 Drawing Sheets

SYSTEM AND METHOD FOR PERFORMING IMAGE-BASED DIAGNOSIS

FIELD OF THE INVENTION

The present invention relates generally to fault diagnosis and more particularly to diagnosing faults from images generated by a malfunctioning imaging machine.

BACKGROUND OF THE INVENTION

In either an industrial or commercial setting, a malfunctioning imaging machine can impair a business severely. Thus, it is essential that a malfunctioning imaging machine be repaired quickly and accurately. Usually, during a malfunction of an imaging machine such as an ultrasound, computed tomography (CT), or a magnetic resonance imaging (MRI) machine, a field engineer is called in to diagnose and repair the machine. Typically, the field engineer looks at an incident record generated from the machine. The incident record contains information such as the type of machine, the modality of the machine, and any customer-related information. In addition, the incident record contains an error log of events that occurred during routine operation as well as during any malfunction situation and any artifact images generated from the machine. Using their accumulated experience at solving machine malfunctions, the field engineer looks through the error log and the artifact images and tries to find any symptoms that may point to the fault. Then the field engineer tries to correct the problem that may be causing the machine malfunction. If the error log contains only a small amount of information, and the generated artifact images are well known, then this process will work fairly well. However, if the error log contains a large amount of imprecise information and the cause of the artifact images is unknown, as is usually the case for large complex devices, then it will be very difficult for the field engineer to quickly diagnose a fault. Therefore, there is a need for a system and method that can quickly diagnose a machine malfunction from a complex error log and artifact images having an unknown cause associated therewith.

SUMMARY OF THE INVENTION

In accordance with one embodiment of this invention, there is provided a system for performing image-based diagnosis. In this embodiment, a database stores a plurality of historical images taken from a plurality of machines. The plurality of historical images comprise a plurality of ideal images generated from the plurality of machines using all possible machine settings. In addition, the plurality of historical images comprise a plurality of artifact images generated from the plurality of machines. Each of the artifact images have known faults associated therewith and a corresponding corrective action for repairing the faults. The system also includes a diagnostic unit for diagnosing a new artifact image from a machine having an unknown fault. The diagnostic unit comprises a diagnostic image processor comprising means for finding an ideal image from the plurality of historical images that most closely matches the new artifact image. An assigning means assigns an artifact category to the new artifact image based on the matched ideal image. An extracting means extracts an artifact feature from the new artifact image according to the assigned category. In addition, there is a diagnostic fault isolator comprising means for generating a plurality of metrics for the extracted artifact feature. An applying means applies the plurality of metrics to identify an artifact image from the plurality of historical images that most closely matches the new artifact image and a corrective action for repairing the unknown fault.

In accordance with a second embodiment of this invention, there is provided a method for performing image-based diagnosis. In this embodiment, a plurality of historical images taken from a plurality of machines are obtained. The plurality of historical images comprise a plurality of ideal images generated from the plurality of machines using all possible machine settings. In addition, the plurality of historical images comprise a plurality of artifact images generated from the plurality of machines. Each of the artifact images have known faults associated therewith and a corresponding corrective action for repairing the faults. A new artifact image from a machine having an unknown fault is then received. An ideal image from the plurality of historical images is found that most closely matches the new artifact image. An artifact category is then assigned to the new artifact image based on the ideal image that most closely matches the new artifact image. A plurality of metrics is then generated for the artifact category assigned to the new artifact image. The plurality of metrics are used to identify an artifact image from the plurality of historical images that most closely matches the new artifact image. In addition, this invention provides a corrective action for diagnosing the unknown fault.

DETAILED DESCRIPTION OF THE INVENTION

Figure 1:
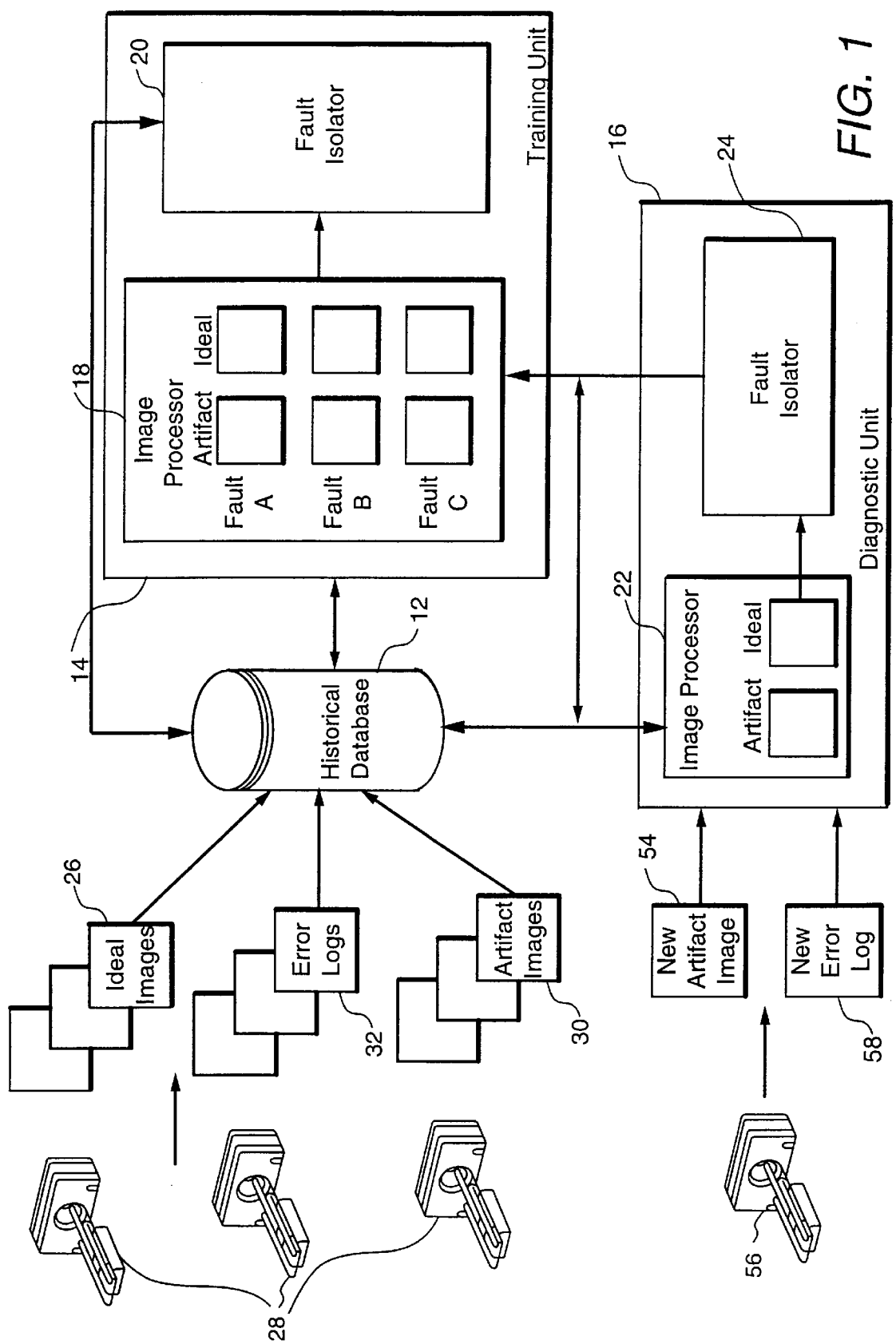
FIG. 1 shows a block diagram of an image-based diagnosis system according to this invention.

The image-based diagnosis system of this invention is described with reference to a medical imaging device such as an ultrasound, CT, or MRI machine. Although this invention is described with reference to a medical imaging device, the image-based diagnosis system can be used in conjunction with any imaging device (chemical, mechanical, electronic, microprocessor controlled) which generates images. FIG. 1 shows a block diagram of an image-based diagnosis system 10 according to this invention. The image-based diagnosis system 10 includes a database 12 of historical images, a training unit 14, and a diagnostic unit 16. The training unit 14 includes an image processor 18 and a fault isolator 20. The diagnostic unit 16 also includes an image processor 22, and a fault isolator 24. Both the training unit 14 and the diagnostic unit 16 are embedded in a computer such as a workstation. However other types of computers can be used such as a mainframe, a minicomputer, a microcomputer, or a supercomputer.

The historical images stored in the database 12 comprise a plurality of ideal images 26 of phantoms generated from a plurality of imaging machines 28. The plurality of ideal images 26 of phantoms are generated from imaging machines using all possible probes and all possible machine default parameter settings. The model of the imaging machine, the probe used, the phantoms that were imaged, and the parameter settings on the imaging machines are inputted along with the ideal images into the database 12 remotely by a field engineer. Alternatively, the machine generating the images may be programmed to put this information in the image file itself, e.g., in the header of the image. Thus, the information becomes an integral part of the database 12. For images acquired remotely, the variables such as the model type, the probe used, and the phantom used, are present in the images themselves and can be automatically extracted later by the training unit 14. However, the parameter settings are not discrete and can potentially take on an infinite combination of continuous values. Accordingly, it is treated different than the other variables. In this invention, the number of machine settings are fixed to a finite set. For example, each ideal image that is acquired from the field is annotated by a field engineer or a technician on-site with the appropriate label specifying the parameter settings of the imaging machine. Examples of some of the parameter settings for an imaging machine are "abdominal setting", "thoracic setting", and "carotid setting".

In addition to a plurality of ideal images 26, the database 12 receives a plurality of artifact images 30 generated from the plurality of imaging machines 28. Each of the artifact images 30 are results of known faults such as unplugging a board, installing a defective board, etc. Like the ideal images 26, each of the artifact images 30 have variables accompanying it such as the model of the imaging machine, the probe used, the phantoms that were imaged, and the parameter settings on the imaging machines. Again the variables such as the model type, the probe used, and the phantom used are present in the images themselves and are automatically extracted, while the parameter settings variable is fixed to a finite set and specified by a field engineer or a technician. Also, the plurality of artifact images 30 and accompanying variables are inputted to the database 12 remotely by a field engineer. Alternatively, the machine generating the artifact images may be programmed to put this information in the image file itself, e.g., in the header of the image.

In addition to the plurality of artifact images 30, the database 12 receives a plurality of error logs and keyboard logs 32 generated from the imaging machines 28. The error logs and keyboard logs each contain a record of events of the imaging machines that occur during routine operation and any malfunction situation. The error logs and keyboard logs represent a signature of the operation of each imaging machine. Each of the error logs and keyboard logs 32 correspond to one of the artifact images 30. For example, one of the error logs and keyboard logs might contain a sequence of events for an imaging machine that has a board unplugged. Another error log and keyboard log might contain a sequence of events for an imaging machine that was installed with a defective board. The plurality of error logs and keyboard logs 32 are stored in the database 12 and are used as historical cases documenting the software and hardware errors occurring at the different imaging machines 28. A description of the processing of the historical cases is described later in more detail.

After the plurality of artifact images 30 and error logs and keyboard logs 32 have been inputted to the database 12, the artifact images are partitioned into a plurality of sets. In particular, the artifact images 30 are partitioned into MxPxFxS sets, wherein M is the number of imaging machines, P is the number of probes, F is the number of phantoms available, and S is the number of machine settings. Since some of the machines cannot handle all of the probes or machine settings there will be some empty sets. Partitioning the artifact images 30 into sets makes it easier to find a historical match for a new artifact image having an unknown fault.

Figure 2:
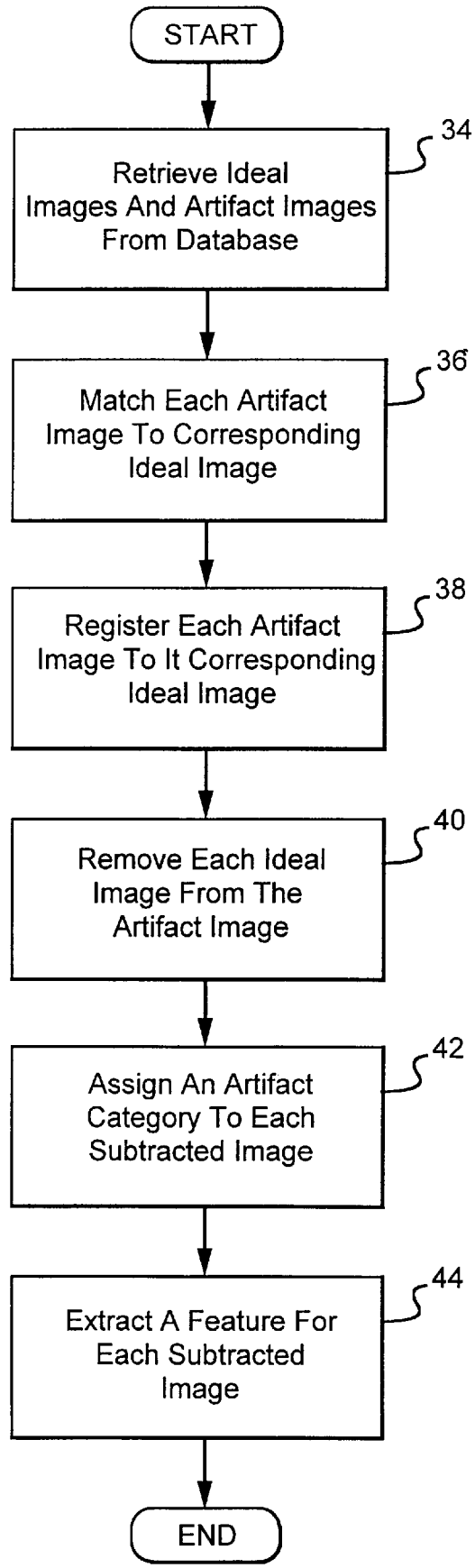
FIG. 2 shows a flow chart setting forth the image processing steps performed by the training unit shown in FIG. 1.

The historical images in the database 12 are accessed by the training unit 14 through the image processor 18. The image processor 18 processes the plurality of ideal images 26 with the plurality of artifact images 30. FIG. 2 shows a flow chart setting forth the image processing steps performed by the image processor 18. The image processing steps begin at 34 where the plurality of ideal images 26 and plurality of artifact images 30 are retrieved from the database 12. Each artifact image is then matched to a corresponding ideal image at 36. The matching process ensures that the machine type, probe, and machine settings are the same for the artifact and ideal images.

For each match, the artifact image is then registered to its corresponding ideal image at 38. Typically, the images are acquired manually by placing a probe from the imaging machine onto a phantom. A result of the manual placement of the probe is that the there is a certain variability in the images from one acquisition to the next. Registration is used to remove the variability as much as possible. Any residual misregistration that remains after registration is taken into account later by the categorization step which is described below. Essentially, the registration enables a pixel by pixel comparison of images acquired at different times. In this invention, registration is achieved by mapping the artifact image to the ideal image. This entails specifying fiducial markers in the artifact images. The image processor 18 then processes the regions of interest covered in the fiducial markers to derive a two-dimensional point that can be matched with the corresponding ideal image. More specifically, the image processor 18 takes the centroid of each fiducial marker and uses it to do point to point matching with the ideal image. Alternatively, it is possible to carry out registration by warping the artifact image to the corresponding ideal image so that there is maximum correlation. The warping may be done via a perspective, affine, or rigid body transformation of one image to match the other image.

After registration, each ideal image is removed from the artifact image at 40. In this invention, the ideal image is removed by using a subtraction operation. The subtraction operation is done pixel by pixel, whereby the gray-level of the ideal image pixel is taken out from that of the artifact image. Since the final image may contain negative numbers after this operation, the subtracted image is renormalized such that the minimum pixel in it is zero. The subtraction operation results in a subtracted image that contains only the artifacts. Alternatively, a filtration operation may be applied to both images before subtraction to account for any residual misregistration between the ideal images and the artifact images.

After subtraction, an artifact category is then assigned to each subtracted image at 42. In this invention, the assigned artifact category is based on an eigen space representation of the subtracted artifact images. The eigen space representation is determined by first computing a covariance matrix. To determine the covariance matrix, each subtracted image is represented by a vector V of pixel values. For an n x m image, the first n values are the n pixels in the first row of the image, the next n values are the pixel values in the second row of the image, and so forth. The given set of N subtracted images are represented by $\{V_1, V_2, \ldots V_N\}$. The average of all of the subtracted images is represented by $V_{avg}$. The covariance matrix is defined by the following equation:

$$cov(i, j) = \frac{(V_i - V_{avg}) \cdot (V_j - V_{avg})}{n \times m}, \text{ wherein} \quad (1)$$

$i,j \in \{1,2, \ldots N\}$ and "●" denotes the dot product.

After the covariance matrix has been determined, it is used to obtain an orthogonal representation and an image basis. The orthogonal representation and image basis are attained by performing a Singular Value Decomposition (SVD) on the covariance matrix. Alternatively, a Karhunen-Loeven Transform (KLT) can be used to determine the orthogonal representation and image basis. The KLT is the statistical equivalent of the SVD and entails diagonalization of the covariance matrix. For a KLT, the covariance matrix is represented by Q and is defined as:

$$Q = UDV^T, \text{ wherein} \quad (2)$$

U and V are orthonormal and D is a diagonal matrix. The columns of V define a new image basis. It is a property of this new basis set that the images in it are uncorrelated. Other less computationally intensive methods may be used to obtain the orthogonal representation and image basis. For example, a discrete cosine transform (DCT) may be used.

The determined image basis is then used to find a representation for each of the subtracted artifact images. In particular, each of the subtracted artifact images are represented as a linear combination of the images in the new basis set. Thus, if $B_1, B_2, \ldots B_N$ are the N basis images, then a historical artifact image I is characterized by the coefficients $\alpha_1, \alpha_2, \ldots \alpha_n$, such that $$I = \alpha_1 B_1 + \ldots + \alpha_N B_N, \text{ wherein} \quad (3)$$

$(\alpha_1, \ldots \alpha_N)$ is a point in the N dimensional space defined by $\{B_1, \ldots B_N\}$. Each subtracted artifact image in the historical database is represented by one such point. After a representation is found for each of the subtracted artifact images, then clusters of closely spaced points in this hyperspace are designated as artifact categories. Some possible examples of designated artifact categories are "Flash light artifacts", "TD board artifacts", "Search light artifacts", and "Distortion artifacts". These examples are illustrative of some of the types of artifact categories that may be used in this invention and is not meant to be exhaustive. For illustration purposes, some of the artifact categories are shown in FIG. 1 as Fault A, Fault B, and Fault C.

After categorization, the image processor 18 extracts a set of artifact features for each of the artifacts at 44. Artifact features are extracted by first converting each artifact image generated from the subtraction operation into the Fourier domain. Converting the artifact images into the Fourier domain results in a spectral signature of the artifacts. Many category-specific features that can be measured, include image homogeneity, signal-to-noise ratio, modulation transfer function, resolution, distortion, signal attenuation, and texture properties. This invention is not limited to these category-specific features and other features can be measured if desired.

Figure 3:
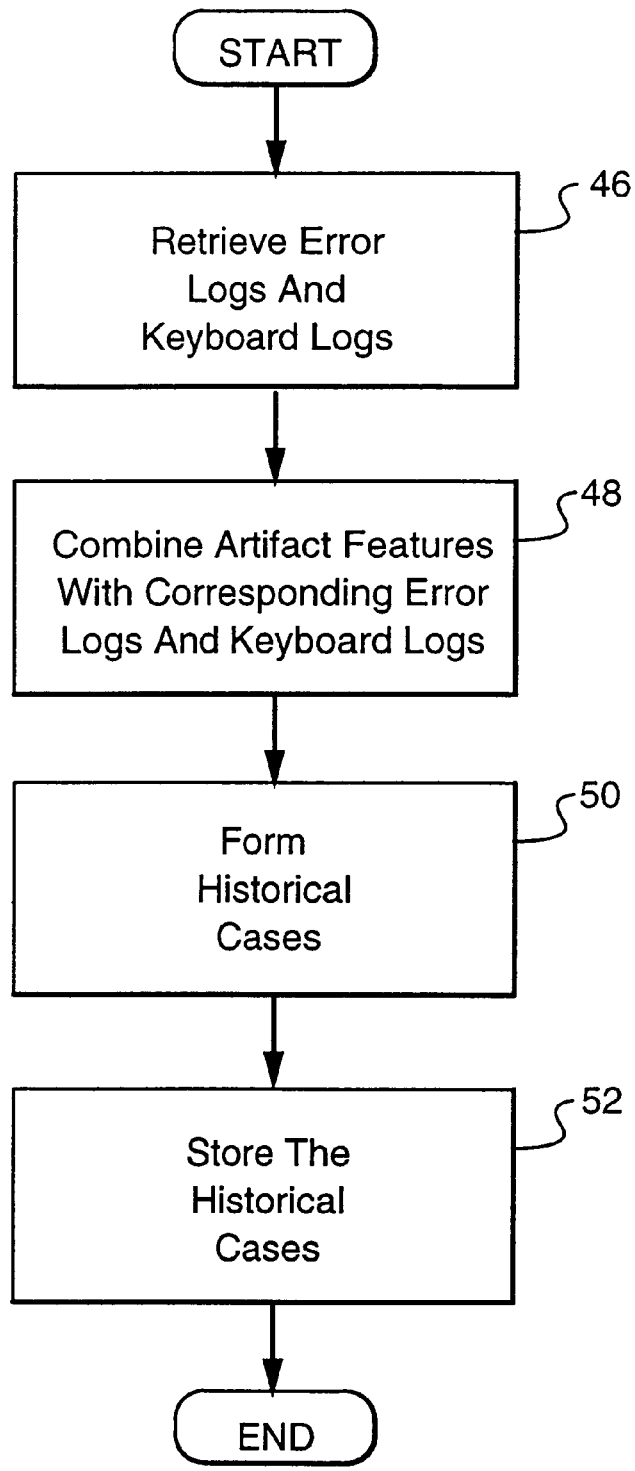
FIG. 3 shows a flow chart setting forth the fault isolation processing steps performed by the training unit shown in FIG. 1.

Referring back to FIG. 2, after the artifact features for all of the artifact images have been determined, the image processor 18 sends the features to the fault isolator 20 for further processing. FIG. 3 shows a flow chart setting forth the processing steps performed by the fault isolator 20.

The fault isolator 20 first retrieves the error logs and keyboard logs 32 from the database 12 at 46. Next, the error logs and keyboard logs 32 are combined with their corresponding artifact features at 48. The features of each artifact, which have been quantified using various category-specific metrics typify the syndrome associated with an actual fault. The error logs and keyboard logs also typify the syndrome associated with the actual fault. These three sources of information are used to generate a case for a case-based reasoning system. Each set of combined artifact features and logs generates a historical case at 50. The historical cases of artifact features and logs are then stored in the database at 52 and used later by the diagnostic unit 16 to diagnose a new problem situation in which there is a new artifact image generated from an imaging machine having an unknown fault.

Referring back to FIG. 1, the diagnostic unit 16 receives a new artifact image 54 generated from an imaging machine 56 experiencing an unknown fault. In addition, a new error log and keyboard log 58 of the events occurring at the imaging machine 56 is sent to the diagnostic unit 16. Both the new artifact image 54 and the new error log and keyboard log 58 are inputted to the diagnostic unit 16 at its image processor 22 by either a field engineer or by a remote dial-in connection. The image processor 22 processes the new artifact image 54 and new error log and keyboard log 56 with the historical cases stored in the database 12.

Figure 4:
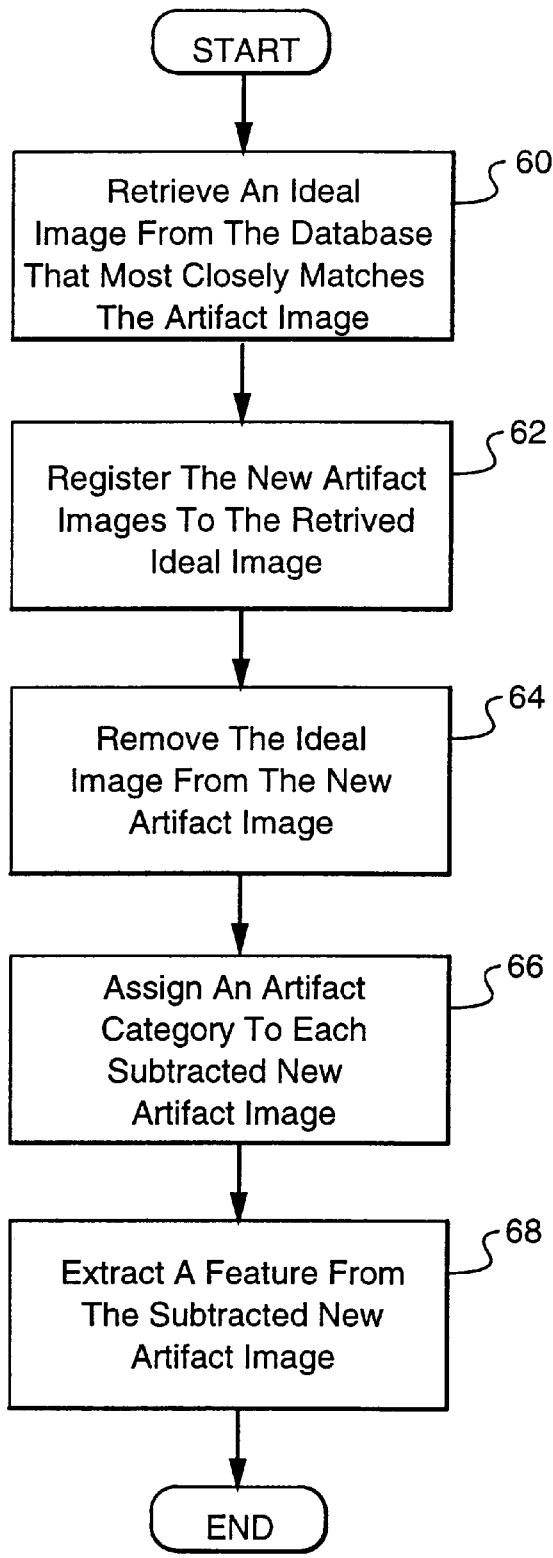
FIG. 4 shows a flow chart setting forth the image processing steps performed by the diagnostic unit shown in FIG. 1.

FIG. 4 shows a flow chart setting forth the image processing steps performed by the image processor 22. After acquiring the new artifact image, the image processor 22 then searches the database 12 and retrieves an ideal image that most closely matches the new artifact image at 60. The image processor then registers the ideal image to the new artifact image at 62. As mentioned above, registration is achieved by mapping the new artifact image to the ideal image by specifying fiducial markers in the new artifact image and processing the markers to derive a two-dimensional point that is matched with the ideal image. After registration, the ideal image is then subtracted from the new artifact image at 64 by using a subtraction or filtration operation. The subtracted image is represented as a linear combination of the same basis set $\{B_1, \ldots B_N\}$ and is defined as:

$$I_{artifact} = \beta_1 B_1, \ldots \beta_N B_N, \text{ wherein} \quad (4)$$

the point $\{\beta_1, \ldots \beta_N\}$ represents another point in the space of historical artifact images. The distance of this point from all of the artifact clusters is used to determine which category the incoming image belongs to. An artifact category is then assigned to the subtracted new artifact image at 66. After an artifact category has been assigned, an artifact feature is then extracted from the subtracted new artifact image at 68 by the image processor 22 in the manner described above.

Figure 5:
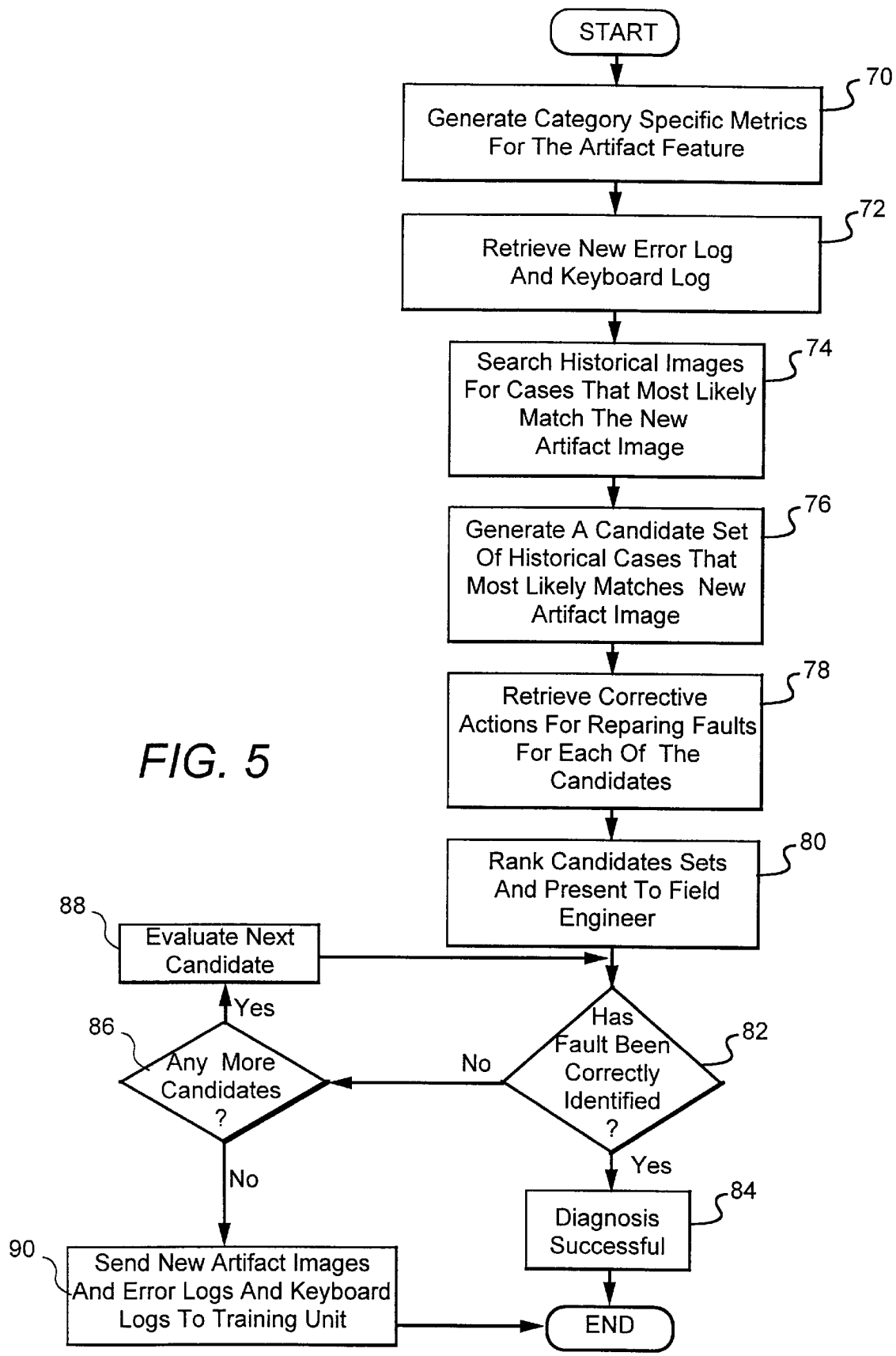
FIG. 5 shows a flow chart setting forth the fault isolation processing steps performed by the diagnostic unit shown in FIG. 1.

After the artifact feature for the new artifact image has been determined, the image processor 22 sends the feature to the fault isolator 24 for further processing. FIG. 5 shows a flow chart setting forth the processing steps performed by the fault isolator 24. The fault isolator 24 uses the extracted artifact feature to generate category specific metrics at 70. The metrics are used to further typify the fault that causes the imaging machine 56 to produce the artifact image 54. Next, the error log and keyboard log 58 accompanying the new artifact image 54 are retrieved at 72. The fault isolator 24 then searches the historical cases in the database 12 at 74 for cases that most likely match the new artifact image. A candidate set of images that most likely match the new artifact image are generated at 76. In addition, corrective actions for repairing the faults corresponding to each of the candidates are retrieved at 78. One type of corrective action may be identifying the field replaceable unit within the imaging machine 56 that needs to be replaced.

The candidate set of images and corresponding corrective actions are ranked in order of their likelihood of matching the new artifact image and presented to a field engineer at 80. The field engineer then goes through the candidate sets in the ranked order at 82 and determines if the fault resulting in the new artifact image has been correctly identified. If the fault has been correctly identified, then the fault isolator 24 logs the diagnosis as successful at 84. On the other hand, if the fault has not been correctly identified, then it is determined whether there are any more candidate sets to evaluate at 86. If there are more candidates, then the next candidate is evaluated at 88 and 82 again. These steps continue until the fault has been correctly identified. However, if none of the candidates correct the fault, then the new artifact image 54 and error log and keyboard log 58 are sent to the training unit 14 at 90 and added to the historical cases for diagnosing future faults. Eventually, as more cases are added to the training unit 14, the image-based diagnosis system's level of accuracy will even out and then it will be unnecessary to add any more cases to the training unit.

It is therefore apparent that there has been provided in accordance with the present invention, a system and method for performing image-based diagnosis that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

What is claimed is:

1. A system for performing image-based diagnosis of a machine, comprising:
    a database containing a plurality of historical images taken from a plurality of machines, the plurality of historical images comprising a plurality of ideal images generated from the plurality of machines using all possible machine settings and a plurality of artifact images generated from the plurality of machines, each of the artifact images having known faults associated therewith and a corresponding corrective action for repairing the faults; and
    a diagnostic unit for diagnosing a new artifact image from a machine having an unknown fault, the diagnostic unit comprising a diagnostic image processor comprising means for finding an ideal image from the plurality of historical images that most closely matches the new artifact image, means for assigning an artifact category to the new artifact image based on the matched ideal image, and means for extracting an artifact feature from the new artifact image according to the assigned category; and a diagnostic fault isolator comprising means for generating a plurality of metrics for the extracted artifact feature and means for applying the plurality of metrics to identify an artifact image from the plurality of historical images that most closely matches the new artifact image and a corrective action for repairing the unknown fault.

2. The system according to claim 1, further comprising a training unit coupled to the database and the diagnostic unit, the training unit comprising a training image processor comprising means for obtaining the plurality of artifact images and the plurality of ideal images, means for matching each of the plurality of artifact images to a corresponding ideal image, means for assigning an artifact category to each match, and means for extracting an artifact feature from each match according to the assigned category.

3. The system according to claim 2, wherein the training image processor further comprises means for registering each of the plurality of artifact images to its matched corresponding ideal image and means for removing each of the corresponding ideal images from its matched artifact image after registration.

4. The system according to claim 2, wherein the training unit further comprises a training fault isolator coupled to the training image processor for isolating the extracted artifact features into historical cases.

5. The system according to claim 4, wherein the database further comprises a plurality of error logs generated from the plurality of machines, each of the plurality of error logs containing data representative of events occurring during operation of the machines.

6. The system according to claim 5, wherein the training fault isolator combines the extracted artifact features and error logs into historical cases.

7. The system according to claim 1, wherein the diagnostic image processor further comprises means for registering the new artifact image to the ideal image that most closely matches the new artifact image and means for removing the corresponding ideal image from the new artifact image after registration.

8. The system according to claim 1, wherein the diagnostic fault isolator comprises means for receiving an error log generated from the machine having the unknown fault, the error log containing data representative of events occurring during operation of the machine.

9. The system according to claim 8, wherein the diagnostic fault isolator uses the error log to generate the plurality of metrics.

10. The system according to claim 1, wherein the diagnostic unit further comprises means for adding newly identified artifact images and corresponding corrective actions to the plurality of artifact images in the database.

11. A method for performing image-based diagnosis of a machine, comprising the steps of:
    obtaining a plurality of historical images taken from a plurality of machines, the plurality of historical images comprising a plurality of ideal images generated from the plurality of machines using all possible machine settings and a plurality of artifact images generated from the plurality of machines, each of the artifact images having known faults associated therewith and a corresponding corrective action for repairing the faults;
    receiving a new artifact image from a machine having an unknown fault;
    finding an ideal image from the plurality of historical images that most closely matches the new artifact image;
    assigning an artifact category to the new artifact image based on the ideal image that most closely matches the new artifact image;
    generating a plurality of metrics for the artifact category assigned to the new artifact image; and
    using the plurality of metrics to identify an artifact image from the plurality of historical images that most closely matches the new artifact image and a corrective action for repairing the unknown fault.

12. The method according to claim 11, wherein the step of obtaining the plurality of historical images comprises the steps of:
    matching each of the plurality of artifact images to a corresponding ideal image taken from the plurality of ideal images;

assigning an artifact category to each match; and extracting an artifact feature from each match.

13. The method according to claim 12, further comprising the steps of:

registering the artifact image with its known fault to the corresponding ideal image; and removing the corresponding ideal image from the registered image.

14. The method according to claim 11, further comprising the step of determining an artifact feature for the new artifact image.

15. The method according to claim 11, further comprising the steps of:

registering the new artifact image to a corresponding ideal image; and removing the corresponding ideal image from the registered image.

16. The method according to claim 11, further comprising the step of adding newly identified artifact images and corresponding corrective actions to the plurality of artifact images in the plurality of historical images.

17. The method according to claim 11, further comprising the step of inputting an error log from the machine having the unknown fault, the error log containing data representative of events occurring during operation of the machines.

18. The method according to claim 17, wherein the inputted error log is used to generate the plurality of metrics for new artifact image.

* * * * *